United States Patent [19]

Erhardt

[11] Patent Number: 4,998,528
[45] Date of Patent: Mar. 12, 1991

[54] TRIGGERING THERAPEUTIC SHOCK WAVES

[75] Inventor: Wolfgang Erhardt, Fuerstenfeldbruck, Fed. Rep. of Germany

[73] Assignee: Dornier Medizintechnik GmbH, Germering, Fed. Rep. of Germany

[21] Appl. No.: 209,688

[22] Filed: Jun. 21, 1988

[30] Foreign Application Priority Data

Jun. 24, 1987 [DE] Fed. Rep. of Germany ....... 3720826

[51] Int. Cl.$^5$ ..................... A61B 5/0205; A61B 17/22
[52] U.S. Cl. ................................... 128/24 A; 128/721
[58] Field of Search ..................... 128/24 A, 718, 721, 128/24 EL; 606/127, 128

[56] References Cited

U.S. PATENT DOCUMENTS

| | | | |
|---|---|---|---|
| 4,059,098 | 11/1977 | Murdock | 128/660.01 |
| 4,237,901 | 12/1980 | Taenzer | 128/660.07 |
| 4,745,920 | 5/1988 | Forssmann et al. | 606/128 |
| 4,811,725 | 3/1989 | Grasser | 128/24 EL |
| 4,834,074 | 5/1989 | Reichenberger | 128/24 EL |

Primary Examiner—Francis Jaworski
Assistant Examiner—Krista M. Pfaffle
Attorney, Agent, or Firm—Ralf H. Siegemund

[57] ABSTRACT

The production of shock-waves is triggered by using the cushion that couples acoustically and, incidentally physically, a shock-wave generator to the body of a living being; any pressure variations in the cushion are detected at a particular phase and used for triggering the generation of shock-waves. The pressure level in the cushion is kept constant, on a long term-basis, and at a level about which breath-induced pressure variations occur.

5 Claims, 3 Drawing Sheets

TRIGGERING THERAPEUTIC SHOCK WAVES

BACKGROUND OF THE INVENTION

The present invention relates to triggering the production and introduction of shock waves into the body of a living being, such as a patient, in synchronism with the breathing of that patient.

German Printed Patent Application 3,146,628 (see also U.S. Pat. No. 4,745,920 and 4,685,461) describes the comminution of concrements by means of shock waves wherein the shock waves are triggered inter alia in response to the breathing of the patient. The purpose is the following. Breathing introduces, from an overall point of view, motion and displacement of organs and parts within the body of that person. This displacement is also effective on concrements such as kidney stones to be comminuted. Hence the location of the concrements varies periodically with the breathing of the person. On the other hand, focusing of shockwaves requires a definite point and locus into which shock waves are to be focused. Therefore the motion of the concrement on the one hand, and the focusing action on the other hand, have to be synchronized, which means that in the course of oscillatory displacement of the concrement on account of breathing, one can establish the locus for the concrement during a particular phase of the breathing cycle, by triggering shockwave generation during one of the next breathing cycles in the same phase point under the assumption that the concrement will have moved back to exactly the same position it had previously during a similar phase within a breathing cycle.

The following are references which refer broadly to this field of art and are of an exemplary nature only. Among thim is also the U.S. Pat. No. 4,539,989 which discloses a device for comminution of concrement in connection with a coupling cushion by means of which the device producing the shock wave is acoustically coupled to the body of the person.

DESCRIPTION OF THE INVENTION

It is an object of the present invention to provide a new and improved device and method for triggering the introduction of shock waves into the body of a human being in synchronism with breathing.

It is a feature of the present invention to provide shock wave triggering in synchronism with breathing without having to employ a respirometer or the like.

It is a further feature of the invention to use a water-filled coupler-cushion being interposed between the body of the patient and the shock wave generator.

In accordance with the preferred embodiment of the present invention, it is suggested to use that coupler-cushion of the type referred to above, in conjunction with a pressure-sensitive transducer monitoring the pressure in that cushion; to process the signal provided by the transducer as representation of the breathing cycles; and to derive from that transducer and from the signal as processed, the trigger-signal for the generation of shock waves. The trigger signal may be used also for triggering x-ray diagnostics; the trigger signal may be combined with another that is derived from an EKG.

Hence the invention uses a secondary effect for tracking the breathing movements of the patient. Actually, the pressure in the coupler-cushion will even better reflect body motions due to breathing if the cushion pressure is controlled (long term) for operating normally at a constant pressure level so that the pressure variations on account of breathing motion are superimposed. This pressure control may be a two- or three-step control or a two- or three-point control, possibly with proportionate, reset and derivative control characteristics.

It is believed that the invention offers the following advantages. Through monitoring the pressure in the coupler cushion, one does in fact broadly ascertain the respiratory cycle of the person, and more specifically, the signal derived from the cushion pressure measuring transducer is a direct representation of any displacement of most organs, including kidneys bearing stones, etc. within the body of the patient on account of his breathing.

It is very interesting that the direct measurement of breathing, through a respirometer, for example, is not necessary. All that is necessary is simply a pressure measurement of the coupler-cushion pressure. The coupling function of the water cushion establishes an immediate motion and pressure sensing device as far as the body of the patient is concerned, and faithfully reproduces this motion as a pressure variation in the coupled cushion. It is that variation which is used for triggering the shock-wave generation in particular timed relationship.

From a practical point of view, then, existing equipment is used, including the coupler-cushion of the kind mentioned above, and all that is necessary is to introduce a pressure-sensing monitor and transducer which is connected to a suitable amplifier, and through relatively simple signal processing, a trigger signal for the shock-wave generation is derived. It has to be observed that shock-wave generation requires some form of trigger signal in any case, which is to be derived from some source. In other words, as far as the shock-wave generation and control is concerned, there is no modification. All that is changed, as per the present invention, is the source for the trigger signal.

A particularly advantageous form of practicing the invention finds the pressure sensor, i.e. its output as being used for controlling the level of pressure and/or for holding the coupling-cushion pressure constant on a long-term basis. In this form, then, one uses the transducer for purposes of an additional function. The control, of course, must not obliterate the variations resulting from the breathing, but makes sure that there is a constant level or zero level in relation to which these pressure variations on account of breathing occur. It is that zero level which is being controlled.

DESCRIPTION OF THE DRAWINGS

While the specification concludes with claims particularly pointing out and distinctly claiming the subject matter which is regarded as the invention, it is believed that the invention, the objects and features of the invention, and further objects, features and advantages thereof will be better understood from the following description taken in connection with the accompanying drawings in which:

Proceeding now to the detailed description of the drawings, FIG. 1 shows a device in which the pressure level control for a coupler-cushion K is combined with breath-cycle detection through common pressure sensing by means of a transducer PT. The pressure sensing output is used in different ranges of variation frequency for purposes of breath-dependent shock wave triggering, as well as for longterm pressure level stabilization.

It is assumed that a rest L, a bed, or the like is provided onto which the body PK of the patient is placed. The rest has an opening $L^1$ and a shock-wave generator SG is placed underneath. The shock-wave generator SG is of the kind referred to above, resulting specifically out of the development of the Assignee corporation.

This shock-wave generator SG provides on each trigger action a shock-wave to be transmitted into the body PK of the person through a coupler-cushion K. The coupler-cushion K is basically filled with water and can be constructed as shown, for example, in Assignee's co-pending application Ser. No. 942,251 filed Dec. 16, 1986 (overlapping inventive entities).

The coupler-cushion K contains the pressure-sensor monitor or transducer PT which is connected to amplifier V whose output is fed to a control circuit C. This circuit C provides suitable adaptation and includes, for instance, a phase detector, a peak detector, or a particular level detector through a peak detector (maximum or minimum) is preferred. That detector provides a narrow width enabling signals an arc generator for the shock wave generator SG particularly for purposes of triggering it. More details about the trigger process will be discussed below.

Additionally, the pressure indicating signal from amplifier V is an input signal for a pressure controller R. The output of controller R is used to control, on the average, the pressure level in the cushion K. The control may obtain basically through amplitude discrimination, i.e. exclusion of low-level variations, while maintaining an average pressure level, possibly under utilization of hysteresis switching.

One way of effecting control is through frequency discrimination; a low pass-filter in the input circuit of controller R eliminates breath-cycle frequency variations so that the controller R responds to quasi-stationary variations only.

Basically, the rest L and the shock-wave generator SG constitute a unit with the cushion K becoming effective whenever a patient rests on the rest L. Coupling obtains by filling the cushion K with a coupler medium such as water. For adjusting the requisite coupling pressure, one obtains a level control for the pressure to be kept constant by the controller R. The output amplifier V being connected to the sensor or transducer PT, is the input for that control. The control may, for example, feed more or less water into the cushion K or discharge some water from the cushion.

Figure 2:
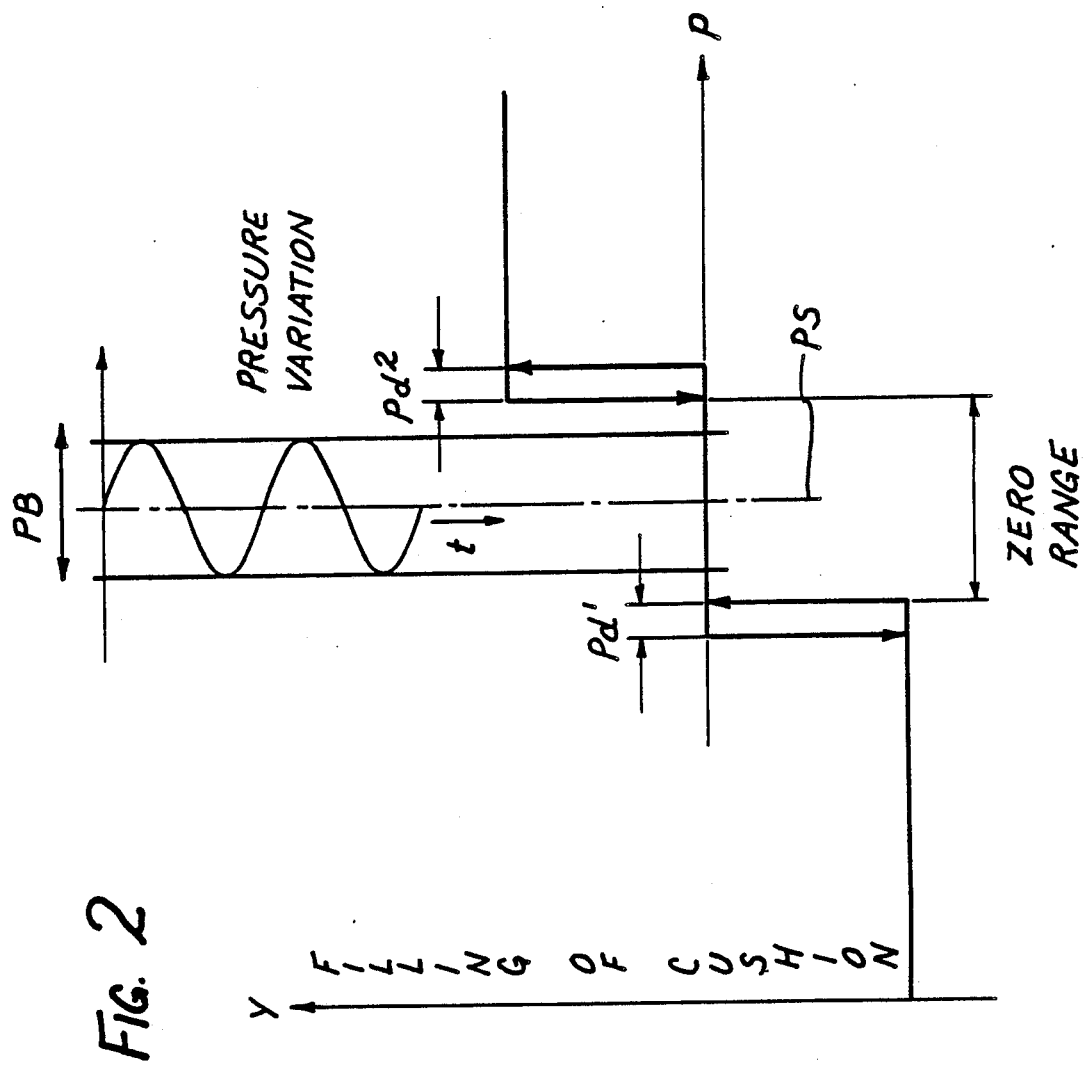
FIG. 2 is a diagram of signals as they are developed within the system shown in FIG. 1.

FIG. 2 shows the dependency of the relationship between the filling and emptying of the cushion K plotted along the Y-axis, and the pressure P in the cushion which is controlled variable. As the cushion K abuts against the patient's body, the pressure increases, and the controller stops the liquid supply. Thereafter the controller operates with a particular hysteresis which, so to speak, brackets a range PB within which the breath-dependent pressure variations occur. Therefore, the controller R will not try to track the pressure variations on account of the breathing and motion of the patient. Rather, it is the level PS around which extends the range PB and in relation to which the breath-dependent pressure variations occur that is being controlled. In a supplemental fashion, the level PS can also be interpreted as a time axis for time t for indicating the cyclic pressure variations that obtain with the breathing cycle.

In accordance with the invention, the electronic signal derived from the pressure-sensor PR is used to ascertain the oscillatory pressure variations in the coupler medium, on account of the breathing of the patient. These variations are limited to the range PB and occur about a zero establishing pressure level PS that is actually the average cushion pressure.

Turning to some details, as stated, PB denotes the pressure variation range in cushion K resulting from breathing. This range may be of the order of 10 mbar. PS is the desired level of pressure, i.e. of coupling pressure in the coupler cushion. The control may be of a fairly simple variety such as switching between two levels, thereby bracketing the average valve and level PS and the switching levels. The switching levels are outside the bracketed range which is the pressure range (PB) within which the breathing-induced pressure variations occur.

Pd1 is the first switching difference of the controller R on the low pressure side. Pd2 is the second switching difference of that controller, and t generally is time. As stated, the pressure controller R operates with particular switching hysteresis within which no control of the pressure obtains. Owing to the breathing of patient-body, the pressure in the coupler medium of cushion K is periodically variable, as shown in FIG. 2. FIG. 2 also shows the limits and these limits are equivalent to the hysteresis range.

It was found now, and this is the main aspect of the invention, that the periodic pressure variations in the coupler medium of the coupler K do not exhibit any phase displacement vis-a-vis the breathing motion, and the frequency was, of course, found to be exactly representative of the respiratory cycle frequency. The zero level and the hysteresis range that is in fact given by the pressure range PB is adjusted in accordance with the invention such that the amplitude of the periodic variations remain within the hysteresis and zero range for the control so that this pressure change will not at all activate the pressure control.

Frequency, phase and amplitude of the periodic pressure variations on account of the breathing, are therefore not changed during normal shock-wave application during which the cushion must, of course, remain in a coupling state to the patient's body that is as invariant as it can possibly be. During this period, then, the pressure variations as detected by the sensor PT are indeed exact replicas of the breathing. The contour of the breathing signal is particularly determined by the output of the amplifier to be used in the evaluating circuit C.

A particular phase within that cycle, and it does not make any difference in principle what phase is chosen, is used to trigger the shock-wave generator. It may be any of the peaks of the pressure variations within pressure range PB. The term phase invariance, means that at a pressure maximum or a minimum, body cavity expansion by the patient is at a maximum or a minimum. Thus, the dislocated concrement is at an extreme position within the moving cycle and is, in fact, at rest for a short period. That is then a convenient instance within which to trigger the shock-wave.

It is important to realize that an additional factor for triggering the shock-wave generator is synchronism with the electrocardiogram so that the triggering proper obtains in conjunction with the breath-dependent trigger signal and a particular signal derived from the EKG which is separately ascertained. In other words shockwave triggering is to coincide with a particular phase of the breathing cycle and also with a particular phase in the heart cycle. Owing to lack of synchronism between EKG and breathing, coincidence is more or less a random phenomenon but it will occur sooner or later.

Figure 3:
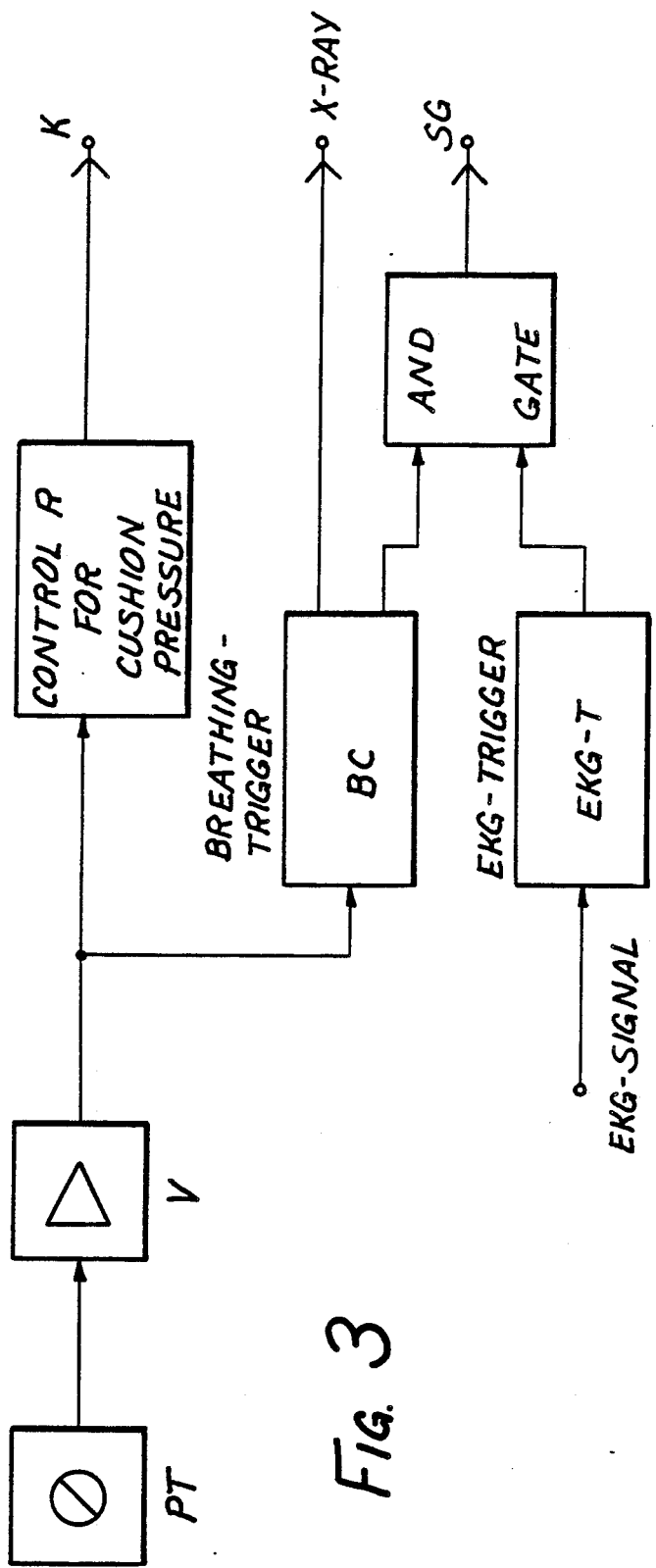
FIG. 3 is a block circuit showing combined EKG and respiratory triggering.

FIG. 3 illustrates such an evaluation. This figure shows how the pressure sensor PT is connected to the amplifier V whose output in turn is also connected to the controller R. The controller R provides directly, as stated above, a pressure control within the coupler-cushion K.

Figure 1:
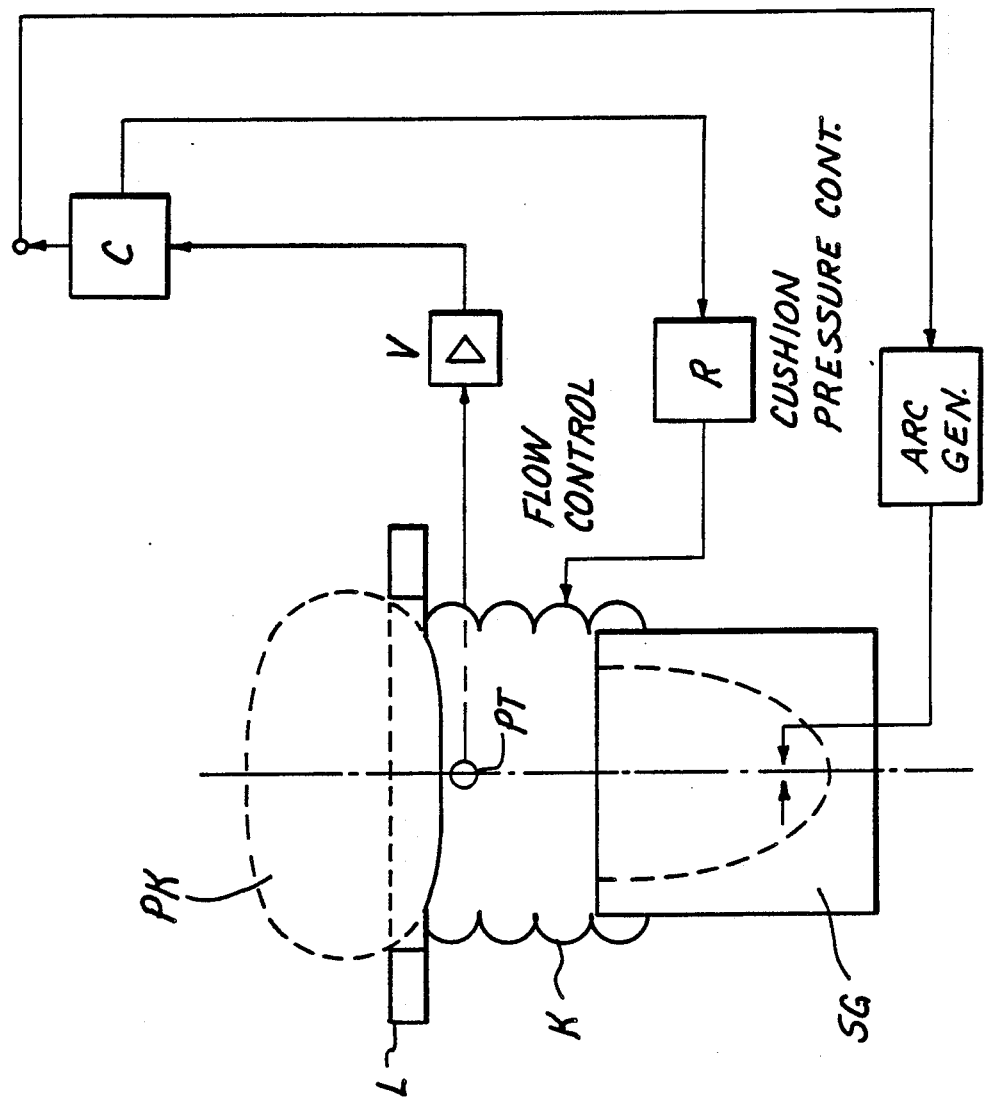
FIG. 1 is a somewhat schematic view of a device for practicing the preferred embodiment of the present invention in accordance with best-mode operational principles.

Also, as was already mentioned above FIG. 1 shows an evaluating circuit 8C for the breath-dependent triggering. In addition thereto thereto, an EKG monitor T is provided for EKG-dependent triggering. The two trigger signals are logically combined and will, on conjunction, trigger shock-waves within a particular phase of breathing; within a particular phase of the EKG signal and on coincidence of these two phases. Please note again that breathing and heart-rate are basically asynchronous events in relation to each other, but sooner or later such a coincidence (overlap) of the trigger signals will occur.

The breath-dependent trigger signal may also be used, for example, for triggering the x-ray diagnostic device as is likewise shown. The advantage of such an arrangement is that all x-ray pictures are again shown take in exactly one and the same phase of the breathing cycle, which means in exactly the same kind of position of the chest cavity, which in turn is an immediate an direct representation of similar positions of the concrement.

The invention is not limited to the embodiments described above; but all changes and modifications thereof, not constituting departures from the spirit and scope of the invention, are intended to be included.

We claim:

1. Method of triggering the production of shock waves for therapy of a living being, comprising the steps of providing a shock wave generator and associated cushion for coupling accoustically said shock wave generator to the body of the living being, detecting cyclic pressure variations in the cushion, the variations being within a range of about 10 mbar and due to breathing cycles of the living being;
    detecting in said cyclic pressure variations a particular phase; and
    repeatedly triggering the production of shock waves by said generator into said cushion in response to the detection of occurrences of said particular phase.

2. Method as in claim 1, including the step of maintaining a particular baseline pressure level in said cushion during the duration of the breathing cycles, said detecting step then comprising detecting said pressure variations superimposed upon said particular baseline pressure level.

3. Method as in claim 1 including the additional step of rendering the triggering dependent on an EKG signal.

4. An apparatus for generating shock-waves including a shockwave generator, a liquid-filled cushion for coupling the shock wave generator to the body of a patient, and a trigger device connected to the shock-wave generator, the improvement comprising:
    a pressure-transducer in the cushion, and means connected to the transducer and to the shockwave generator for deriving from the transducer a trigger signal for triggering the shock-wave generator for generating a shock wave through said cushion to the body of said patient.

5. An apparatus as in claim 4, including control means connected to the transducer for monitoring the average pressure in the cushion to establish a particular pressure level around which pressure variations occur on account of breathing of the patient.

* * * * *

UNITED STATES PATENT AND TRADEMARK OFFICE
CERTIFICATE OF CORRECTION

PATENT NO. : 4,998,528

DATED : March 12, 1991

INVENTOR(S) : Othmar Wess, Reiner Groezinger, Wolfgang Erhardt

It is certified that error appears in the above-identified patent and that said Letters Patent is hereby corrected as shown below:

On the title page, item (19) should read-- Erhardt, et al.--

Item (75) Othmar Wess and Reiner Grozinger should be added.

Signed and Sealed this

Second Day of June, 1992

Attest:

DOUGLAS B. COMER

*Attesting Officer*　　*Acting Commissioner of Patents and Trademarks*